United States Patent

Wong

[11] Patent Number: 5,631,420
[45] Date of Patent: May 20, 1997

[54] HYDROMETER

[76] Inventor: Tommy Chi-Kin Wong, 2/F,36 Lung Sum Avenue, Sheung Shui N.T., Hong Kong

[21] Appl. No.: 677,834

[22] Filed: Jul. 10, 1996

[51] Int. Cl.⁶ .................................................. G02N 9/00
[52] U.S. Cl. .................................................. 73/454; 73/451
[58] Field of Search .................................. 73/32 R, 437, 73/444, 445, 446, 448, 450, 451, 452, 454

[56] References Cited

U.S. PATENT DOCUMENTS

| | | | |
|---|---|---|---|
| 1,432,773 | 10/1922 | Midgley, Jr. | 73/454 |
| 3,340,736 | 9/1967 | Suematsu | 73/454 |
| 4,037,481 | 7/1977 | Callahan | 73/454 |
| 4,353,253 | 10/1982 | Callahan | 73/454 |
| 4,697,454 | 10/1987 | Lu | 73/454 X |

*Primary Examiner*—Elizabeth L. Dougherty
*Attorney, Agent, or Firm*—Jacobson, Price, Holman & Stern, PLLC

[57] ABSTRACT

A hydrometer includes a liquid container defining a measuring chamber. A pointer is pivotally mounted inside the measuring chamber and adapted for indicating the specific gravity of a liquid sample contained in the measuring chamber. The liquid container is mounted with a concealed liquid sample intake pipe adapted for picking up the liquid sample to be measured and delivering the liquid sample to the measuring chamber. The concealed liquid sample intake pipe has a bottom open end extending out of the lowest side of the liquid container and a top open end suspending in the measuring chamber above the upper limit liquid level.

1 Claim, 3 Drawing Sheets

HYDROMETER

BACKGROUND OF THE INVENTION

1. Field of the Invention

The present invention relates to a hydrometer for measuring the specific gravity of liquids, and relates more particularly to such a hydrometer which has a concealed pipe convenient for picking up a liquid sample to be measured.

2. Description of the Related Art

Regular hydrometers are commonly comprised of a liquid container having a top opening and defining a measuring chamber, and a pointer pivotably mounted inside the measuring chamber. When in use, the liquid container is dipped in the liquid, permitting the liquid to flow into the inside of the measuring chamber through the top opening of the liquid container. Alternatively, a liquid pick-up device may be used to pick up the liquid and to fill the liquid into the measuring chamber. When the liquid to be measured is filled in the measuring chamber of the liquid container, the pointer is forced by the liquid to displace, and therefore the specific gravity of the liquid is measured. The drawback of this structure of hydrometers is that the operators hands tend to be contaminated by the liquid.

FIG. 3 shows another structure of hydrometer according to the prior art. This hydrometer comprises a liquid container 3, a pointer 4, a hand pump 5, and a suction tube 6. The pointer 4 is pivotably mounted inside the liquid container 3. The liquid container 3 has a water passage 31 on the inside. The hand pump 5 is mounted on the liquid container 3 at the top and connected to the top end of the water passage 31. The suction tube 6 is connected to the bottom end of the water passage 31 outside of the liquid container 3. When in use, the suction tube 6 is dipped in the liquid, then the hand pump 5 is operated to draw the liquid into the suction tube 6, permitting the liquid to be guided through the water passage 31 into the inside of the liquid container 3. This structure of hydrometer is complicated, and expensive to manufacture. Furthermore, the external parts, namely, the suction tube 6 and the hand pump 5 tend to be damaged.

SUMMARY OF THE INVENTION

It is one object of the present invention to provide a hydrometer which has liquid sample pick-up means adapted for picking up the liquid to be measured without causing the operator's hand to be contaminated. It is another object of the present invention to provide a hydrometer which is simple and inexpensive to manufacture. According to the preferred embodiment of the present invention, the hydrometer comprises a liquid container defining a measuring chamber, and a pointer pivotably mounted inside the measuring chamber and adapted for indicating the specific gravity of the liquid sample contained in the measuring chamber, wherein the liquid container is mounted with a concealed liquid sample intake pipe adapted for picking up the liquid sample to be measured and delivering it to the measuring chamber, the concealed liquid sample intake pipe having a bottom open end extending out of the lowest side of the liquid container and a top open end suspending in the measuring chamber above the upper limit liquid level.

DETAILED DESCRIPTION OF THE PREFERRED EMBODIMENT

Figure 1:
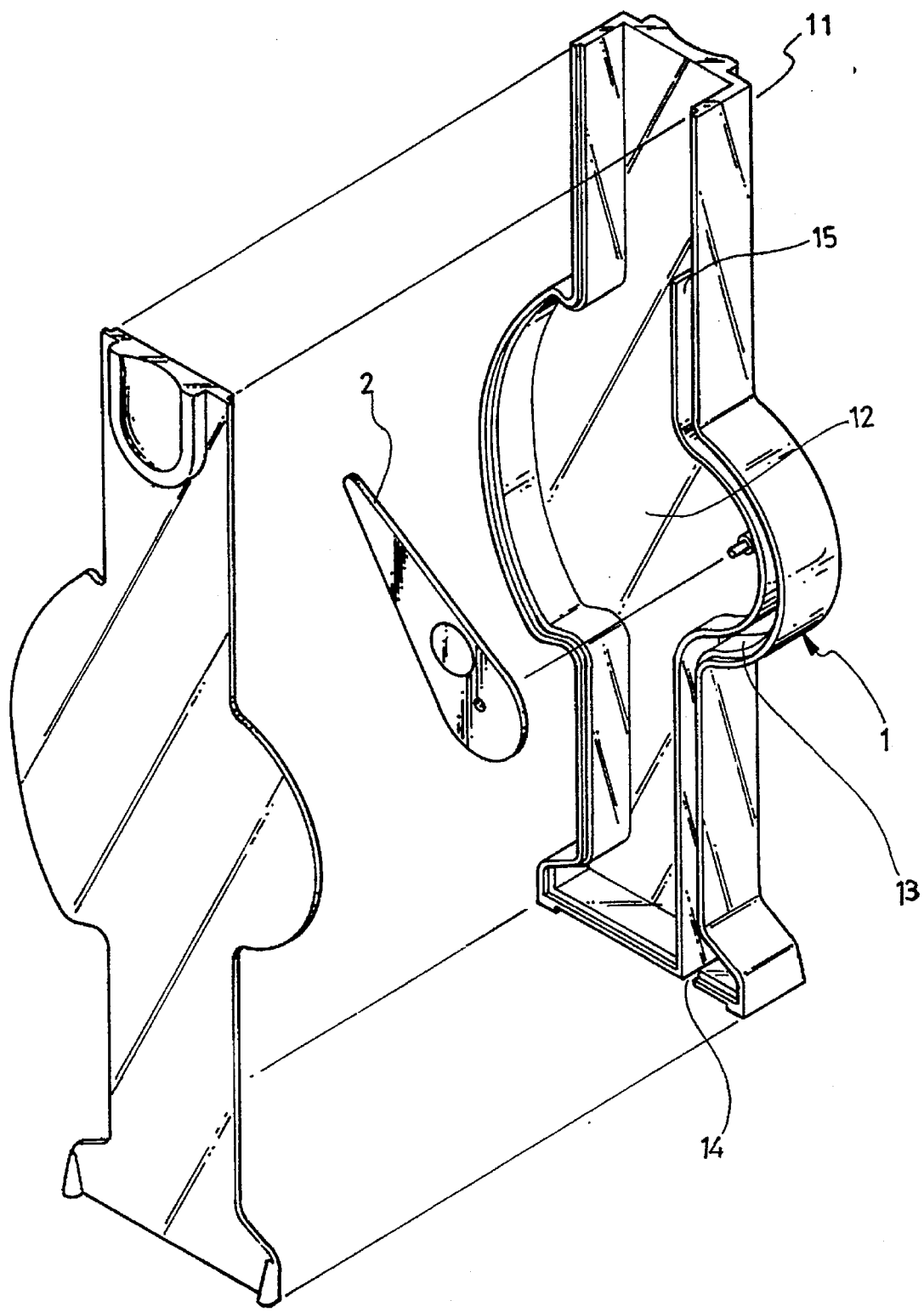
FIG. 1 is an exploded view of a hydrometer according to the present invention.
Figure 2:
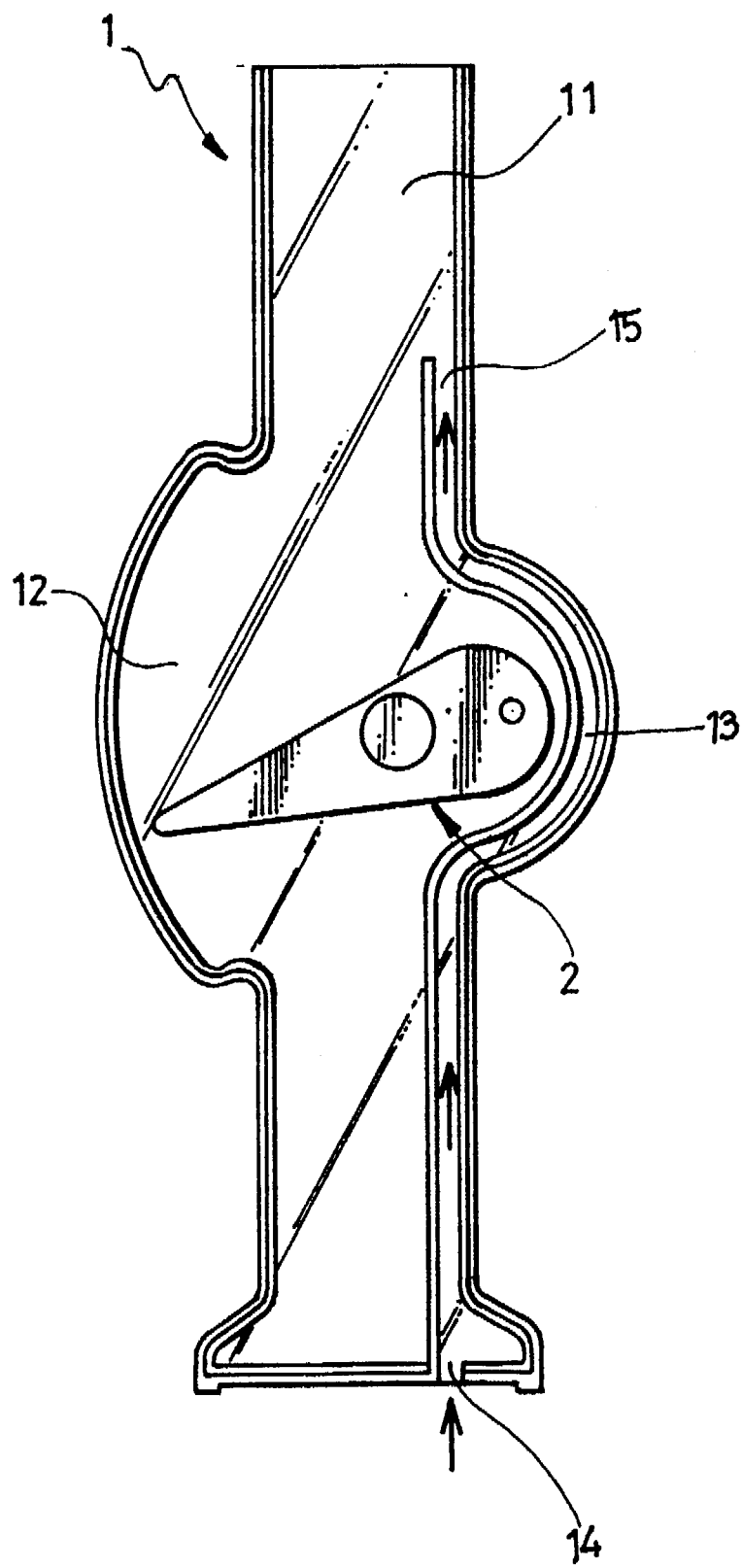
FIG. 2 is a sectional view of the present invention.
Figure 3:
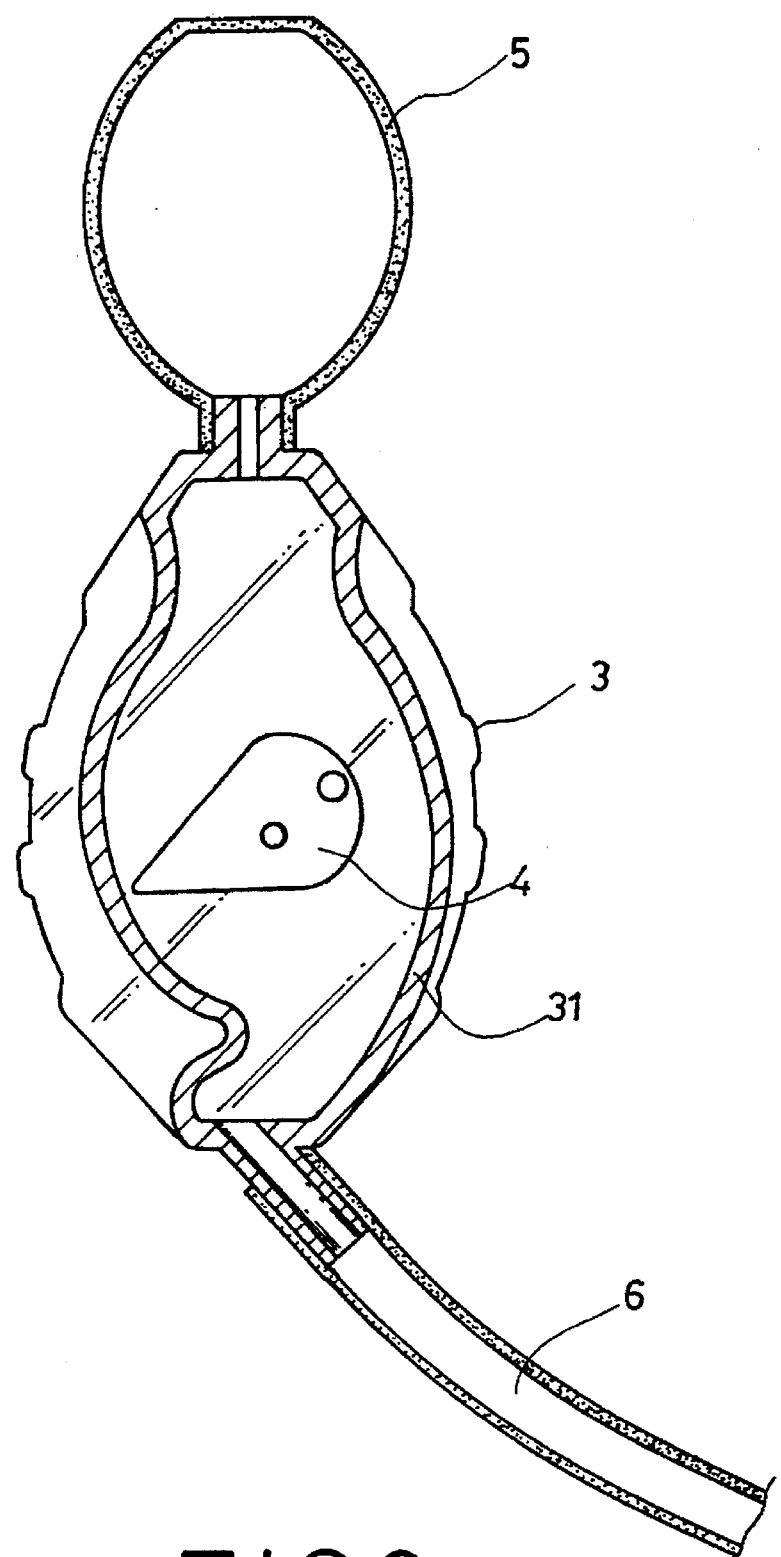
FIG. 3 is a schematic drawing showing the structure of a hydrometer according to the prior art.

Referring to FIGS. 1 and 2, a hydrometer in accordance with the present invention is generally comprised of a liquid container 1, and a pointer 2 pivotably mounted in the liquid container 1 and floated in the liquid sample contained in the liquid container 1 to indicate the specific gravity of the liquid sample. The liquid container 1 comprises a handle 11 at the top, a measuring chamber 12 at the bottom, and a concealed liquid intake pipe 13 adapted for picking up a liquid sample and delivering it to the measuring chamber 12 for measuring. The concealed liquid sample intake pipe 13 has a bottom open end 14 extending out of the bottom side of the liquid container 1, and a top open end 15 suspending inside the measuring chamber 12 above the upper limit liquid level. By dipping the liquid container 1 in the liquid to be measured with the bottom open end 14 of the concealed liquid sample intake pipe 13 facing downwards, the liquid is forced to flow from the bottom open end 14 of the concealed liquid sample intake pipe 13 through the top open end 15 thereof into the inside of the measuring chamber 12 to force the pointer 2 to displace and to indicate the specific gravity of the liquid.

While only one embodiment of the present invention has been shown and described, it will be understood that various modifications and changes could be made without departing from the spirit and scope of the invention disclosed.

What the invention claimed is:

1. A hydrometer comprising a liquid container, said liquid container having a handle at a top side thereof, and a measuring chamber at a bottom side thereof for containing a liquid sample to be measured and having an upper limit liquid level defining an upper limit at which the measuring chamber may contain the liquid sample, and a pointer pivotally mounted inside said measuring chamber for indicating the specific gravity of the liquid sample contained in said measuring chamber, wherein said liquid container comprises a concealed liquid sample intake pipe, having a bottom open end extending out of the lowest side of said liquid container and a top open end located in said measuring chamber above said upper limit liquid level, for picking up the liquid sample to be measured at the bottom open end and delivering it to said measuring chamber through the top open end.

* * * * *